United States Patent [19]

Van der Knaap

[11] Patent Number: Plant 6,240

[45] Date of Patent: Aug. 2, 1988

[54] CHRYSANTHEMUM PLANT NAMED DAYMARK

[75] Inventor: Jacques C. M. Van der Knaap, De Lier, Netherlands

[73] Assignee: Fides, Handelskwekerij, De Lier, Netherlands

[21] Appl. No.: 821,536

[22] Filed: Jan. 22, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Daymark particularly characterized by its anemone capitulum; white ray floret color; yellow-green to yellow disc florets which become petaloids, and by its low temperature tolerance.

1 Drawing Sheet

The present invention comprises a new and distinct cultivar of Chrysanthemum, botanically known as *Dendranthema morifolium,* Ramat., previously *Chrysanthemum morifolium,* Ramat., and referred to by the cultivar name Daymark.

Daymark is a product of a planned breeding program which had the objective of creating new Chrysanthemum cultivars with anemone capitulum, white ray floret color, 8 week response, low temperature tolerance, and the ability to produce commercially acceptable quality in year around cut mum programs. Such traits in combination were not present or needed improvement in previously available commercial cultivars.

Daymark was originated from a hybridization made in a controlled breeding program in De Lier, The Netherlands in 1981. The female parent was Refour, an unpatented cultivar. The male parent of Daymark was a first generation hybrid between the cultivar Oriette and an unnamed paternal parent. Daymark was discovered and selected as one flowering plant within the progeny of the stated cross by Jacques C. M. Van der Knaap in June of 1982, in a controlled environment in De Lier, The Netherlands.

The first act of asexual reproduction of Daymark was accomplished when vegetative cuttings were taken from the initial selection in July of 1982 in a controlled environment in De Lier, The Netherlands by a technician working under formulations established and supervised by Jacques C. M. Van der Knaap. Horticultural examination of selected units initiated in November of 1982 has demonstrated that the combination of characteristics as herein disclosed for Daymark are firmly fixed and are retained through successive generations of asexual reproduction.

Daymark has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Daymark which, in combination, distinguish this Chrysanthemum as a new and distinct cultivar:

1. Anemone capitulum.
2. Single capitulum type.

3. White ray floret
4. Yellow-green (immature) to yellow (mature) disc florets.
5. Disc florets become petaloids.
6. Low temperature tolerance.

Of the many commercial cultivars known to the present inventor, the most similar in comparison to Daymark is the female parent Refour. In comparison to Refour, Daymark has more vigor, larger leaves, a larger flower size and less of a white cushion in the center of the flower. The ray floret color and capitulum form and type of Daymark are similar to those same characteristics of Refour.

The accompanying photographic drawing shows typical inflorescence and foliage characteristics of Daymark, the color photogrpahs being as true as reasonably possible for photographs of this type.

In the following description, color references are made to The Royal Horticultural Society Colour Chart. The color values were determined between 11:00 a.m. and 12:00 noon in November of 1982 under natural day light at De Lier, The Netherlands.

Classification:

*Botanical.*—*Dendranthema morifolium,* Ramat., cv Daymark.

*Commercial.*—Cut anemone spray.

INFLORESCENCE

A. Capitulum:

*Form.*—Flat.

*Type.*—Anemone.

*Diameter across face:*—45–74 mm.

B. Corolla of ray florets:

*Color (general tonality from a distance of three meters).*—White.

*Color (upper surface).*—RHS 155D.

*Color (under surface).*—RHS 155D.

C. Corolla of disc florets:

*Color (mature).*—Primarily 155D (on outer petaloids to near center), also showing varying shades of green near center, including 150C.

*Color (immature).*—Various shades of dark green in center, including 146C, lightening radially outwardly to various shades including 150C, and white 155D at outer periphery.

D. Reproductive organs:

*Androecium.*—Present in disc florets; numerous.

*Gynoecium.*—Present in both disc and ray florets; numerous.

PLANT

A. General appearance:
Height.—85 cm.

B. Foliage:
*Color (upper surface).*—RHS 147A.

*Shape.*—Short lobed and serrated.

I claim:

1. A new and distinct Chrysanthemum plant named Daymark, as described and illustrated, and particularly characterized by its anemone capitulum; white ray floret color; yellow-green to yellow disc florets which become petaloids, and by its low temperature tolerance.

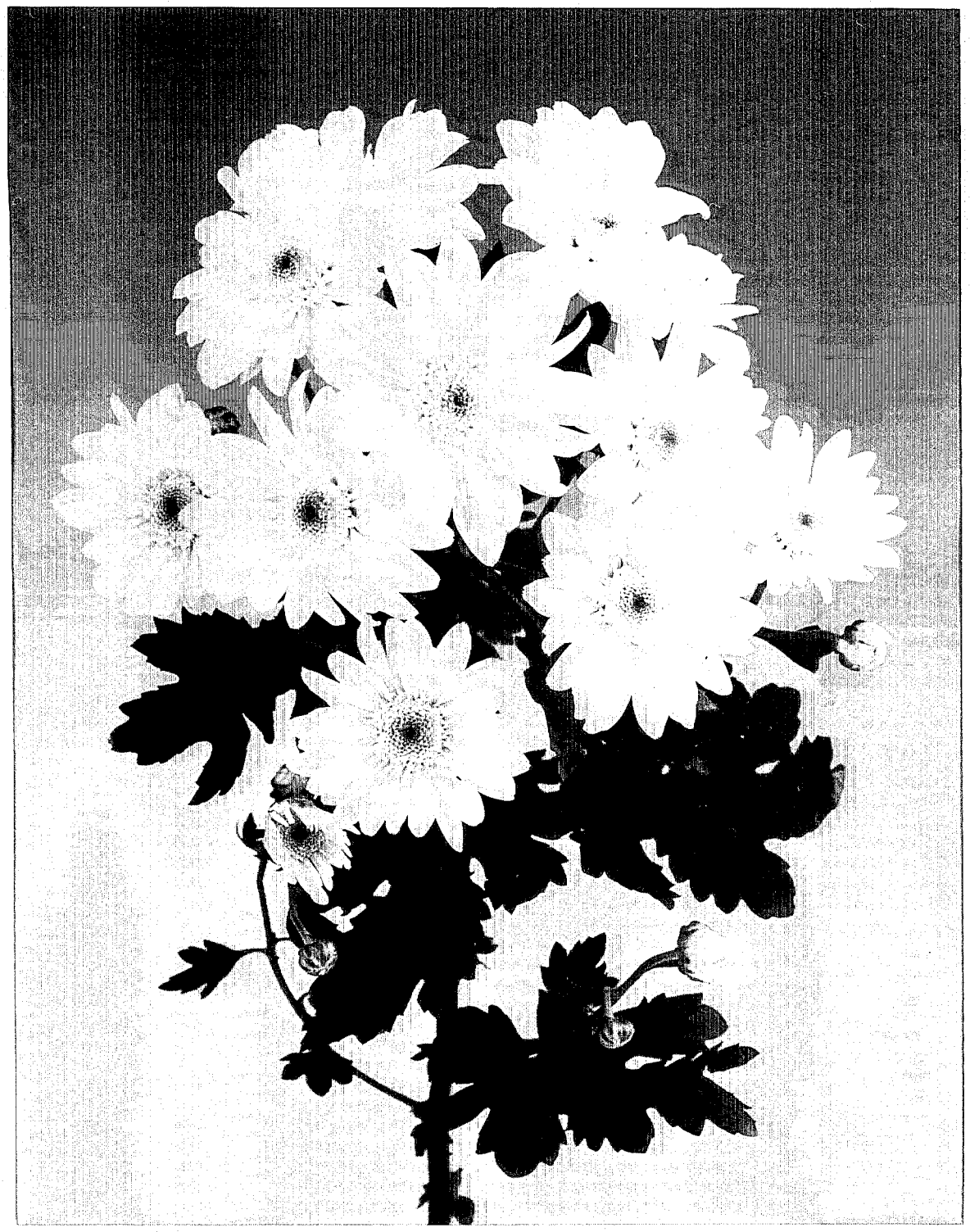

* * * * *